United States Patent
Bulinski

(10) Patent No.: US 6,596,475 B2
(45) Date of Patent: *Jul. 22, 2003

(54) PROTEIN CONJUGATES CONTAINING MULTIMERS OF GREEN FLUORESCENT PROTEIN

(75) Inventor: Jeannette Chloe Bulinski, Leonia, NJ (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/834,352

(22) Filed: Apr. 12, 2001

(65) Prior Publication Data

US 2001/0055767 A1 Dec. 27, 2001

Related U.S. Application Data

(63) Continuation of application No. PCT/US99/23918, filed on Oct. 14, 1999, which is a continuation-in-part of application No. 09/172,368, filed on Oct. 14, 1998, now Pat. No. 5,985,533.

(51) Int. Cl.[7] .......................... C12Q 1/00; C12N 15/63; C12N 15/11; C07K 19/00
(52) U.S. Cl. ........................ 435/4; 435/320.1; 530/350; 536/23.4
(58) Field of Search ....................... 435/6, 69.7, 320.1; 536/23.4; 530/350

(56) References Cited

U.S. PATENT DOCUMENTS 5,985,577 A * 11/1999 Bulinski

OTHER PUBLICATIONS

Romoser et al, Detection in Living Cells of Ca2+ –dependent Changes in the Fluorescence Emission of an Indicator Composed of Two Green Fluorescent Protein Variants Linked by a Calmodulin–binding Seq., 1997, The Jour. of Bio. Chem, vol. 272, pp 13270–13274.*

Ludin et al, Application of novel vectors for GFP–tagging of proteins to study microtubule–associated proteins, 1996, Gene, vol. 173, pp. 107–111.*

* cited by examiner

Primary Examiner—John S. Brusca
(74) Attorney, Agent, or Firm—John P. White; Cooper & Dunham LLP

(57) ABSTRACT

This invention provides a vector comprising a nucleic acid which encodes a polypeptide of interest linked to one or more nucleic acid segments encoding at least two Green Fluorescent Proteins. Provided is the method for detecting a polypeptide of interest in a living cell which comprises: (a) transfecting the living cell with an isolated nucleic acid which encodes the polypeptide of interest linked to at least two Green Fluorescent Proteins. Additional polypeptides different from the polypeptide of interest may also be linked to at least two molecules of Green Fluorescent Protein; (b) culturing the transfected cell in conditions permitting expression of Green Fluorescent Protein and the polypeptide of interest; and (c) detecting the fluorescence of the Green Fluorescent Protein, thereby detecting the polypeptide of interest in a cell.

8 Claims, 3 Drawing Sheets

TC-7 ENSCONSIN-GFP-B1

0 sec 30 sec 90 sec 120 sec 140 sec 180 sec 200 sec 210 sec

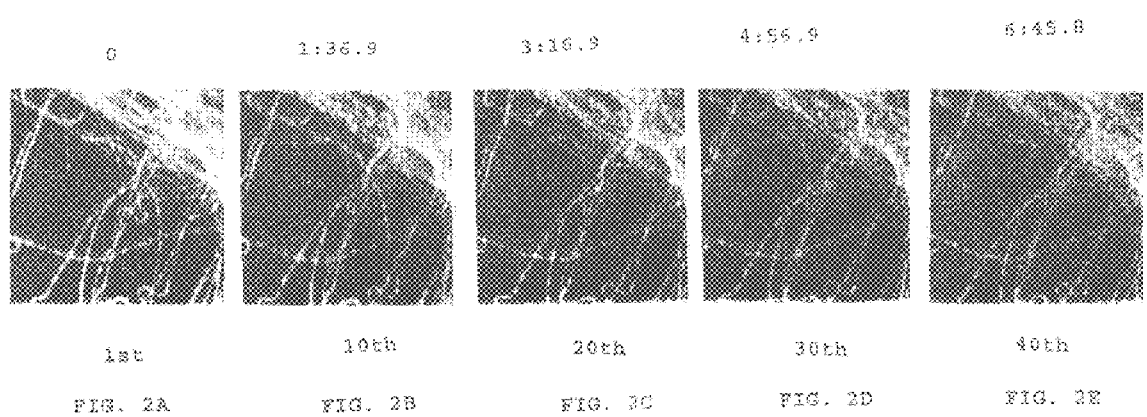

FIG. 3A  
2XGFP-EMTB
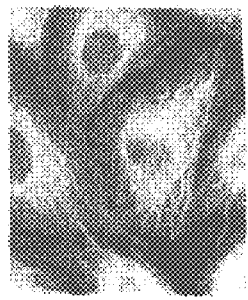
FIG. 3B  
3XGFP-EMTB
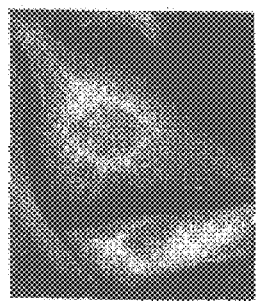
FIG. 3C  
4XGFP-EMTB
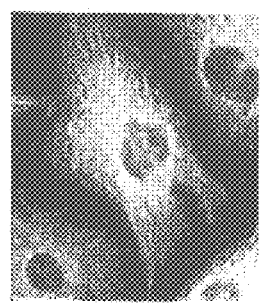
4XGFP-EMTB
peripheral region
FIG. 3D
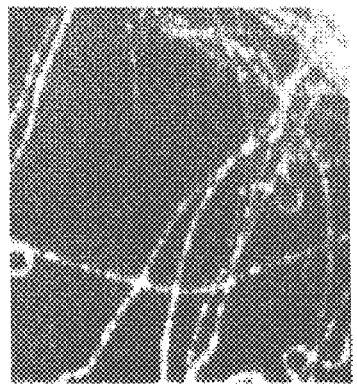
perinuclear
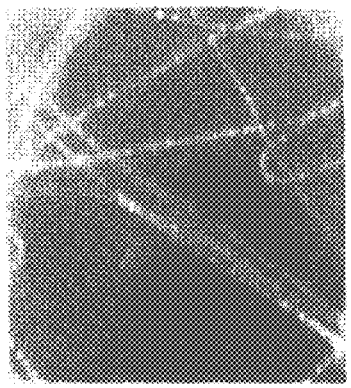
FIG. 3E

PROTEIN CONJUGATES CONTAINING MULTIMERS OF GREEN FLUORESCENT PROTEIN

This application is a continuation of PCT International Application No. PCT/US99/23918, filed Oct. 14, 1999, designating the United States of America, which is a continuation-in-part and claims priority of U.S. Ser. No. 09/172,368, filed Oct. 14, 1998, now U.S. Pat. No. 5,985,577 issued Nov. 16, 1999, the contents of which are hereby incorporated by reference into the present application.

The invention disclosed herein was made with Government support under NIH Grants Nos. CA 70951, GM 24364 and AR 08316. Accordingly, the U.S. Government has certain rights in this invention.

Throughout this application various references are referred to within parenthesis. Disclosures of these publications in their entireties are hereby incorporated by reference into this application to more fully describe the state of the art to which this invention pertains. Full bibliographic citation for these references may be found at the end of this application, preceding claims.

BACKGROUND OF THE INVENTION

In order to follow the dynamics of single cellular microtubules in living cells using time-lapse imaging, expression at high levels of Green-Fluorescent Protein linked to the microtubule associated protein were required. Traditional Green Fluorescent Protein labeling methods induced artifacts such as micro-tubule bundling, mitotic abnormalities, photo bleaching (Heim, et al., 1996) (Cormack et al., 1996) and on/off blinking (Dickson et al, 1997). These labeling induced changes in cell morphology limits the usefulness of traditional Green Fluorescent Protein labeling in vivo.

This invention discloses a method for observing in vivo dynamics and function critical for many cellular processes in living cells using a Green Fluorescent Protein chimeric molecule (GFP-Ensconsin) to provide a non-perturbing label of cellular components.

This invention discloses that the Green Fluorescent Protein chimeric molecule produces a strong stable fluorescence signal useful in labeling individual protein components making them visible for quantitation by fluorescence speckle microscopy and time lapse imaging.

SUMMARY OF THE INVENTION

This invention provides a vector comprising an isolated nucleic acid which encodes a nucleic acid segment of interest linked to one or more nucleic acid segments encoding at least two Green Fluorescent Proteins.

This invention provides a method for detecting a polypeptide of interest in a living cell which comprises: (a) transfecting the living cell with an isolated nucleic acid which encodes the polypeptide of interest linked to at least two Green Fluorescent Proteins. Additional polypeptides different from the polypeptide of interest may also be linked to at least two molecules of Green Fluorescent Protein; (b) culturing the transfected cell in conditions permitting expression of Green Fluorescent Protein and the polypeptide of interest; and (c) detecting the fluorescence of the Green Fluorescent Protein, thereby detecting the polypeptide of interest in a cell.

BRIEF DESCRIPTION OF THE FIGURES

FIG. 1A Time-lapse photos showing greater than 200 molecules Ensconsin per micron microtubule. Here Ensconsin is linked to a single GFP molecule. Time=0 seconds FIG. 1B Time-lapse photos showing greater than 200 molecules Ensconsin per micron microtubule. Here Ensconsin is linked to a single GFP molecule. Time=30 seconds FIG. 1C Time-lapse photos showing greater than 200 molecules Ensconsin per micron microtubule. Here Ensconsin is linked to a single GFP molecule. Time=90 seconds FIG. 1D Time-lapse photos showing greater than 200 molecules Ensconsin per micron microtubule. Here Ensconsin is linked to a single GFP molecule. Time=120 seconds FIG. 1E Time-lapse photos showing greater than 200 molecules Ensconsin per micron microtubule. Here Ensconsin is linked to a single GFP molecule. Time=140 seconds FIG. 1F Time-lapse photos showing greater than 200 molecules Ensconsin per micron microtubule. Here Ensconsin is linked to a single GFP molecule. Time=180 seconds FIG. 1G Time-lapse photos showing greater than 200 molecules Ensconsin per micron microtubule. Here Ensconsin is linked to a single GFP molecule. Time=200 seconds FIG. 1H Time-lapse photos showing greater than 200 molecules Ensconsin per micron microtubule. Here Ensconsin is linked to a single GFP molecule. Time=210 seconds FIGS. 2A. 2B. 2C. 2D. 2E. Green Fluorescent Protein (GFP) linked to each Ensconsin molecule (4x GFP-EMTB). Individual bright spots are molecules of the protein of interest. The protein of interest is present in a concentration of 20–30 molecules per micron of microtubules. The GFP is the mutant form pEGFP-N1. Note that the images are bright after many photographic exposures. For details see text.

FIG. 2A Time-lapse photos showing approximately 20–30 molecules per micron of microtubules linked to 4 GFP molecules. Time=0 seconds FIG. 2B Time-lapse photos showing approximately 20–30 molecules per micron of microtubules linked to 4 GFP molecules. Time=1 minute 36.9 seconds FIG. 2C Time-lapse photos showing approximately 20–30 molecules per micron of microtubules linked to 4 GFP molecules. Time=3 minutes 16.9 seconds FIG. 2D Time-lapse photos showing approximately 20–30 molecules per micron of microtubules linked to 4 GFP molecules. Time=4 minutes 56.9 seconds FIG. 2E Time-lapse photos showing approximately 20–30 molecules per micron of microtubules linked to 4 GFP molecules. Time=6 minutes 45.8 seconds FIGS. 3A. 3B. 3C. 3D. 3E. Multiple copies of Green Fluorescent Protein (GFP) used to label Ensconsin. A portion of the protein of interest (microtubule-binding domain of Ensconsin) (EMTB) is labeled with one, 2 (2x), 3 (3x), 4 (4x) molecules of GFP. The protein is bound to the microtubules. The GFP is pEGFP-N mutant.

FIG. 3A 2 GFP molecules linked to a nucleic acid segment of interest.

FIG. 3B 3 GFP molecules linked to a nucleic acid segment of interest.

FIG. 3C 4 GFP molecules linked to a nucleic acid segment of interest.

FIG. 3D 4 GFP molecules linked to a nucleic acid segment of interest. A high magnification view. The bright spots are made of 1–10 molecules of GFP-EMTB.

FIG. 3E 4 GFP molecules linked to a nucleic acid segment of interest. A High magnification view. The bright spots are made of 1–10 molecules of GFP-EMTB.

DETAILED DESCRIPTION OF THE INVENTION

Figure 1A:
FIGS 1A. 1B. 1C. 1D. 1E. 1F. 1G. 1H. Traditional Green Fluorescent Protein (GFP) labeling is shown. A portion of the protein of interest (microtubule-binding domain of Ensconsin) (EMTB) labeled with one GFP molecule is shown. An increased amount of EMTB protein (greater than 200 molecules Ensconsin per micron of microtubule) is shown. Cells normally containing approximately 50 molecules Ensconsin per microtubule, were used to obtain these images. No satisfactory images could be obtained using a lesser amount of protein. The increased EMTB protein damaged microtubules and caused abnormal cell division. Arrows indicate changes in the microtubule. For details see text.

This invention provides an isolated nucleic acid which encodes a nucleic acid segment of interest linked to one or more nucleic acid segments encoding at least two Green Fluorescent Protein. As used herein, the term nucleic acid segment of interest encompasses any nucleic acid molecule or segment. In an embodiment, the nucleic acid segment encodes an amino acid sequence, polypeptide or protein. In a further embodiment, the protein or polypeptide are found within a cell.

The nucleic acid segments which encode Green Fluorescent Protein are linked at both the 3' and the 5' ends of the nucleic acid of interest, at only the 3' end of the nucleic acid of interest or at only the 5' end of the nucleic acid of interest. In addition, the nucleic acid segments each of which encodes a Green Fluorescent Protein can both be linked to a portion of the nucleic acid segment of interest. As used herein, the term linked encompasses covalent bonding and structural incorporation with a nucleic acid of interest.

This invention also provides an isolated nucleic acid wherein the nucleic acid segment of interest is linked to at least three nucleic acid segments which encode the Green Fluorescent Protein.

As used herein the Green Fluorescent Protein includes but is not limited to a GFP mutant, GFPmut1 (pEGFP-N1). This invention also encompasses fluorescent proteins having the same or similar fluorescence ability as provided by the Green Fluorescent Protein. The Green Fluorescent Proteins linked can be the same or different.

In one embodiment of this invention the isolated nucleic acids are DNA. The isolated nucleic acids are useful for the development of vectors for the study of the cell development. The vector includes but is not limited to a plasmid.

The nucleic acid segment of interest in this invention may encode the cytoskeletal proteins. The cytoskeletal protein includes full-length Ensconsin (E-MAP-115). In another embodiment, the segment encodes the microtubule-binding domain of Ensconsin (EMTB).

This invention also provides a polypeptide which is encoded by the above described nucleic acid.

This invention also provides a protein conjugate containing at least two molecules of the Green Fluorescent Protein and a protein of interest.

A method for detecting the nucleic acid segment of interest requires transfecting the living cell with an isolated nucleic acid comprising a nucleic acid which encodes the nucleic acid segment of interest linked to at least two nucleic acids encoding Green Fluorescent Protein. The transfected cell is cultured in conditions permitting expression of Green Fluorescent Protein and the nucleic acid segment of interest and detecting the Green Fluorescent Protein, thereby detecting the nucleic acid segment of interest in the cell.

The method for detection includes but is not limited to fluorescence speckle microscopy, time lapse imaging, or any fluorescence detection device.

The nucleic acid segment of interest or portion thereof is normally expressed by the cell. The minimum number of molecules of the nucleic acid segment of interest detected is between one and ten.

A method for detecting the nucleic acid segment of interest requires transfecting the living cell with an isolated nucleic acid comprising a nucleic acid which encodes the nucleic acid segment of interest and another nucleic acid which encodes at least two molecules of Green Fluorescent Protein. The transfected cell is cultured in conditions permitting expression of Green Fluorescent Protein and the nucleic acid segment of interest and detecting the Green Fluorescent Protein, thereby detecting the nucleic acid segment of interest, its movement and dynamics in the cell.

In order to investigate the in vivo behavior and potential functions of the cytoskeletal protein Ensconsin (E-MAP-115), cDNA encoding Green Fluorescent Protein (GFP) was linked to full-length Ensconsin (GFP-Ensc) or to its microtubule-binding domain (GFP-EMTB); expressing these constructs allows for visualization of the distribution of Ensconsin (E-MAP-115) in living cells.

A high level of expression of the chimeric GFP-EMTB protein was necessary in order to image individual microtubules, and GFP-Ensc expression or lower level expression of GFP-EMTB was insufficiently sensitive as a label. To study in vivo behavior of Ensconsin (E-MAP-115) in abnormal cells is undesirable. Increasing the fluorescence of individual Ensconsin molecules by fusing microtubule binding domain to multiple GFP molecules allows for observation in vivo of normal cellular structure.

GFP has proven to be an extremely useful tag in studying protein localization and behavior. The prior uses and development of GFP is described in U.S. Pat. No. 5,491,084 incorporated herein by reference. Since GFP from *Aequorea victoria* exhibits only a minor absorption peak at 470 nm, the fluorescence intensity detected using standard fluorescein isothiocyanate (FITC) filters is less than optimal. Many researchers have either truncated or introduced mutations into GFP in attempts to alter the rate of formation of the fluorophore or its absorption/emission properties. Although most of the truncations and mutations result in significant loss of fluorescence, GFP variants with shifts in emission color, increased fluorescence intensity, and decreased sensitivity to photobleaching have been isolated (Heim et. al., 1996). In this invention preparation of GFP constructs, a GFP mutant, GFPmut1 (pEGFP-N1), was used. This mutant has a double mutation; F64L and S65T, which results in a shift of the absorption peak yielding a fluorescence intensity approximately 35 fold higher than GFP with excitation at 488 nm (Cormack et al., 1996) as well as decreased sensitivity to photobleaching.

Figure 1B:
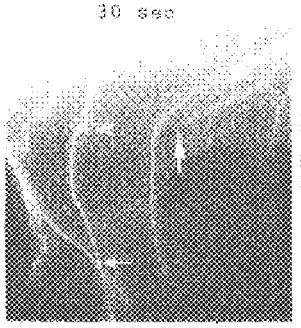
Figure 1C:
Figure 1D:
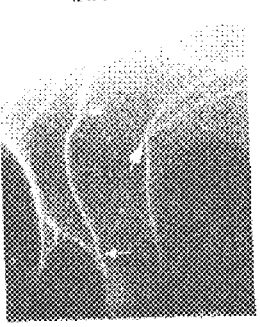
Figure 1E:
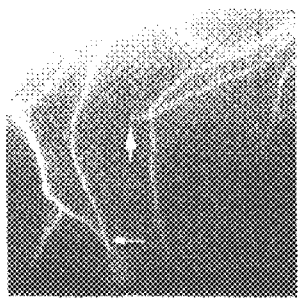
Figure 1F:
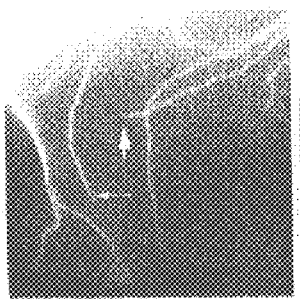
Figure 1G:
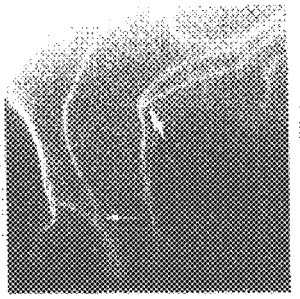
Figure 1H:

Although its two mutations have endowed pEGFP-N1 with properties superior to those of GFP, the amount of signal detectable from this GFP variant can be limiting and is experiment dependant. Additional problems encountered with traditional GFP tagging are photobleaching and blinking/switching associated with long-term imaging. For example, significant photobleaching can preclude capture of more than 10–20 images of the GFP-tagged molecules (FIG. 1)

The GFP molecule is relatively intolerant to mutations and truncations, necessitating an alternate approach to increase the fluorescence of individual GFP-chimeric proteins. By linking multiple GFP molecules in tandem to the nucleic acid segment of interest, these problems could be mitigated. In this manner, a lower amount of protein would be required to yield the same level of fluorescence and would also result in fewer molecules of protein bound. Cells expressing low levels of either 2X- or 3X-GFP-protein were amenable to extensive time-lapse imaging with less profound effects resulting from photobleaching. Another predicted benefit of the tandem linkage of multiple GFP molecules to protein is to average out the effects of blinking over multiple GFP molecules during long term observations (FIG. 2).

This invention will be better understood from the Experimental Details which follow. However, one skilled in the art will readily appreciate that the specific methods and results discussed are merely illustrative of the invention as described more fully in the claims which follow thereafter.

Experimental Details

Preparation of GFP-Ensconsin Constructs

Oligonucleotide primers were used to amplify fragments of cDNA clones encoding appropriate portions of Ensconsin (E-MAP-115) in order to generate plasmids encoding GFP-tagged Ensconsin chimeras of either the full-length molecule (GFP-Ensc) or its microtubule (MT)-binding domain (GFP-EMTB). The plasmid, pGFP-Ensc was made using a full-length E-MAP-115 cDNA as template (Masson and Kreis, 1993) and oligonucleotide primers corresponding to nt 151–166 for the 5' primer and 2309–2329 for the 3' primer and inserting this PCR product into peGFP-NI. To prepare the plasmid, pGFP-EMTB, PCR was also used; the same 5' primer was paired with a 3' primer corresponding to nucleotides 932–952. The primers, all contained HindIII and BamhI restriction sites in the 5' and 3' primers, respectively. PCR conditions for these amplifications were as follows: 94° C. for 30 sec, 50° C. for 30 sec, 72° C. for 1 min, for a total of 30 cycles. PCR products were excised from agarose gels, purified using Geneclean and each was cloned into the HindIII and BamHI restriction enzyme sites of pEGFP-N1.

In order to prepare a plasmid encoding the MT-binding domain of Ensconsin conjugated to two GFP molecules (2X-GFP-EMTB), a 3' primer that corresponded to nucleotides 1381–1400 of pEGFP-N1, but with an added SacII restriction site, was used with the same EMTB 5' primer described above. GFP-EMTB was the template used to amplify sequences encoding the MT-binding domain of Ensconsin along with the GFP moiety. The plasmid, p2X-GFP-EMTB, was generated by cloning this PCR fragment in frame into naïve pEGFP-N1 using the HindIII and SacII restriction enzyme sites.

In order to link the MT-binding domain of Ensconsin to three GFP molecules (3X-GFP-EMTB), PCR was performed again using GFP-EMTB as the template along with 5' primer and 3' primers corresponding to nucleotides 935–949 of Ensconsin and 1390–1407 of pEGFP-N1, respectively. The 3' primer was modified in order to obviate the stop codon and restriction enzyme sites were also added to both primers: KPNI and SacII sites in the 3' primer and SacII and EcoRV sites in the 5' primer. The PCR product was cloned into the SacII restriction site of p2X-GFP-EMTB to produce the plasmid, p3X-GFP-EMTB (FIGS. 3A and 3B).

To generate a plasmid, p4X-GFP-EMTB, which encoded four GFP molecules linked in tandem to EMTB, PCR was again performed with primers that corresponded to nucleotides 935–949 of Ensconsin and 1384–1396 of pEGFP-N1, respectively, to amplify GFP-encoding sequences from pGFP-EMTB. In this case an EcoRV site was introduced into both primers (FIGS. 3C, 3D and 3E).

In order to verify that each additional GFP-encoding cassette was cloned in the proper reading frame, we sequenced all newly created junctions. To sequence the junctions, each plasmid (p2X-, p3X-, and p4X-GFP-EMTB) was digested with BsiHKAI and the appropriate fragment (~720 bp) was purified from an agarose gel, blunt-ended with T4 DNA polymerase and subcloned into the SMAI site of pBluescript. To assure that all junctions had been obtained, individual clones were isolated and digested to check for the presence of a specific site, unique to each junction, that had been introduced via the PCR primer. Individual cDNA clones were isolated and both strands were sequenced using the T7 and T3 promoters using T7 Sequenase Version 2.0 DNA Sequencing Kit.

Preparation of Stable Cell Lines Expressing GFP Chimeric Proteins

TC-7 cells were transfected with pGFP-Ensc, pGFP-EMTB, p2X-GFP-EMTB, p3X-GFP-EMTB, p4x-GFP-EMTB, or pEGFP-N1 lacking a cDNA insert, exactly as described in Nguyen et al. (1998) except that 15 µl of Lipofectamine was used. Cells were viewed in a fluorescence microscope 36–48 hr after transfection to assess efficiency of the transfection procedure, and were then grown in the presence of geneticin (G418) for at least 3 weeks in order to generate stable cell lines. G418-resistant colonies were isolated using cloning cylinders.

Immunological Analysis

Polyclonal antibodies were raised in guinea pigs. Antigen was prepared by subcloning the MT-binding domain of Ensconsin (EMTB) into pRSETA and purifying the recombinant His-tagged protein on TALON beads according to the manufacturers instructions. Immunoblot analysis was performed as described previously (Chapin and Bulinski, 1991a), except that immunoblots were labeled with a $\frac{1}{2000}$ dilution of guinea pig anti-EMTB. Quantification of expression of GFP-chimeric proteins on immunoblots was performed using methods described previously (Chapin and Bulinski, 1991b). HeLa cell extracts were used as a standard for comparison, since the abundance of tubulin and Ensconsin in these extracts has been studied extensively (e.g., Bulinski and Borisy, 1979; Chapin and Bulinski, 1991b).

Immunofluorescence of fixed cells cultured on coverslips was performed exactly as described in Bulinski and Bossler (1994), except using image capture and manipulation procedures described in Nguyen et al., 1997. In some cases, cells were pre-extracted for 4 minutes at 37° C. in 80 mM PIPES, pH 6.8, 5 mM EGTA, 1 mM $MgCl_2$, 0.5% Triton-X 100.

Analysis of mitotic index was determined using two different procedures. Naïve TC-7 cells were compared with those expressing EMTB chimeras. Cells in log phase cultures were fixed in methanol and stained with anti-tubulin antibody and DAPI; cells with condensed chromosomes and mitotic spindles ere scored as a proportion of total cells, keeping in mind hat the fixation and staining steps in the procedure depleted all cultures of the less adherent mitotic cells. To compare Tc-7 cells that expressed different GFP-EMTB chimeras with each other rather than with naïve TC-7 cells, mitotic index was scored using GFP fluorescence to identify cells in mitosis and confirming the state of chromosome condensation with phase microscopic observation.

Imaging of MTs in Living Transfected Cells

Cells plated on glass coverslips were imaged as described in Waterman-Storer et al., 1997. For analysis of drug-treated cells, each coverslip was placed in a perfusion chamber described in Block et al. (1991), and medium containing or lacking nocodazole was introduced. Dual time-lapse imaging and processing of images were performed as described by Waterman-Storer et al. (1997). MT dynamics were quantified in naïve TC-7 cells or stable transfectants expressing GFP-EMTB chimeras as described by Waterman-Storer and Salmon (1997). Briefly, cells growing on glass coverslips were microinjected with porcine brain tubulin labeled with X-rhodamine succinimidyl ester and imaged with a sensitive imaging system that allowed minimal extraneous background fluorescence, maximal efficiency of light collection, and a high quantum efficiency camera, as outlined in Salmon et al. (1998). Time-lapse images of X-rhodamine were collected along with images of GFP fluorescence, if present, using Metamorph software. The parameters of the microtubuledynamics were determined using RTM custom software (Walker et al., 1988) as described in Waterman-Storer and Salmon (1997).

Green Fluorescent Protein Chimeric Proteins and Production of Stable Cell Lines

To ascertain the function(s) of the MAP Ensconsin (E-MAP-115), expression was by chimeric plasmids in which Ensconsin coding sequences were fused to GFP in pEGFP-N1 in African green monkey kidney TC-7 cells. Cells transfected with pEGFP-Ensc or pEGFP-EMTB and subjected to selection with G418 (geneticin) yielded cells that expressed the full-length protein and cells that expressed just the MT-binding domain, respectively. In both fusion proteins, the GFP moiety is located at the carboxy terminus of the protein. We produced clonal cell lines expressing each construct because, for many experiments using these cells, we needed to analyze a uniform population of cells whose content of EGFP-Ensc or EGFP-EMTB was approximately constant and could be accurately determined relative to endogenous MAP or tubulin.

Initial observations of live cells expressing either GFP-Ensc (TC-7-GFP-Ensc cells) or GFP-EMTB (TC-7-GFP-EMTB cells) revealed green fluorescence on cytoplasmic fibers that appeared to be MTs; we verified that the GFP fluorescence indeed coincided with MTs by comparing GFP fluorescenc to anti-tubulin immunofluorescence. Labeling of MTs with GFP-Ensc and GFP-EMTB demonstrated that appending a GFP moiety onto the C-terminus of either MAP molecule did not compromise its ability to bind to Mts. In contrast, addition of an EMTB prevented binding to MTs.

Results document that GFP-chimeras are sufficiently fluorescent to be detected in live cell imaging and were amenable to analysis of Ensconsin/MTB behavior in vivo. The MT localization observed appears to be identical to immunofluorescence of endogenous or transfected full-length Ensconsin (E-MAP-115) or EMTB molecules that do not contain a GFP moiety and the localization pattern of GFP-EMTB in TC-7 cells was unchanged by detergent extraction. This result is consistent with previous immunofluorescence results (Masson and Kreis, 1993; Bulinski and Bossler, 1994). GFP-EMTB is localized along the length of MTs in live and detergent extracted cells. MAP4, another assembly promoting MAP, is localized to MTs in fixed cells and is extracted from MTs with detergent. These results demonstrate that the behavior of the GFP-Ensc and GFP-EMTB chimeras mimic that of the endogenous MAP.

Previous immunofluorescent staining and biochemical assays had been used to determine that the distribution of Ensconsin (E-MAP-115) changed during M-phase (Masson and Kreis, 1995). In contrast, both GFP-Ensc and GFP-EMTB remained associated with MTs throughout the cell cycle, including all stages of mitosis. For example, GFP-Ensconsin chimeras were localized to mitotic spindles in live cells at metaphase, anaphase and late anaphase, respectively. We also examined the distribution of GFP-EMTB under conditions similar to those used for the immunofluorescence studies (Masson and Kreis, 1995). In agreement with the localization pattern in live cells, GFP-EMTB remains associated with mitotic spindles in fixed cells throughout M-phase, as well as in detergent-extracted cells. It is plausible that the previous inability to detect spindle association of Ensconsin was a result of fixation artifacts or the sensitivity of the antibody used for these experiments. It is also possible that our results differ because of the presence of the GFP tag. We note both GFP-Ensc, containing the full-length molecule and including sites of potential mitosis-specific regulation by phosphorylation and GFP-EMTB, which lacks the sites suspected of phosphorylation (Masson and Kreis, 1995), behaved identically, remaining associated with spindle MTs throughout M-phase.

It was important to rule out the possibility that MTs might exhibit artifactual changes in behavior when they possessed bound GFP-Ensc or GFP-EMTB. Cells in which single MTs could be imaged best exhibited a high level of expression of the GFP-chimera. Capturing multiple images of single MTs in cells with lower level expression of Ensconsin or EMTB proved to be difficult or impossible because the fibers were not sufficiently fluorescent. Negative consequences of high level expression of GFP-chimeras included the appearance of bundled MTs. In addition, we noted that during the selection of cell clones, highly expressing cells appeared to die out, raising the possibility that they did not grow very well.

The interaction of Ensconsin (E-MAP-115) with MTs during mitosis was previously shown to be regulated by phosphorylation during M-phase (Masson and Kreis, 1995). High levels of expression of GFP-EMTB might affect the speed or efficacy of mitosis. Compared to naïve TC-7 cells, TC-7-GFP-EMTB cells showed a higher mitotic index; that is, cells expressing high levels of EMTB spent more time in mitosis than control cells. In addition, cells were assayed for abnormalities in M-phase, by scoring the percentage of spindles that were multipolar, rather than bipolar. By this measure, the TC-7-GFP-EMTB cells were also compromised by their level of expression, in their proportion of multipolar spindles compared to control cells. A high concentration of chimeric protein induced artifactual MT behavior.

Increasing the fluorescent signal of individual Ensconsin molecules by preparing EMTB conjugated in tandem to multiple GFP molecules. These constructs, which encoded two, three or four GFP molecules linked to the C-terminus of EMTB (p2X-GFP-EMTB, p3X-GFP-EMTB and p4X-GFP-EMTB, respectively), were introduced into TC-7 cells and clonal cell lines were produced as previously described. In this way, MTs with comparatively lower levels of bound Ensconsin could be imaged under conditions where MT dynamics and cell behavior might not be perturbed. Cells that expressed 2X-,3X-, and 4X-GFP-EMTB, possessed brightly fluorescent cytoplasmic MTs. As determined with western blots, the bright MTs in the three new types of cells did not result from a high level of expression of the EMTB proteins. When expression level was examined with clones of cells expressing 2X-, 3X-, and 4X-GFP-EMTB, relative to the level in GFP-EMTB cells, 2X-lines expressed 10–20% as much GFP-EMTB, and 3x-and 4x-lines expressed 20% as much. Thus, bright MTs did not arise at the expense of highly abnormal over expression of chimeric molecules.

Examination of TC-7 cells expressing the EMTB constructs bearing the tandomly repeated GFP moiety revealed fluorescent MTs indistinguishable from the arrays observed by immunofluorescence or microinjection in naïve, non-transfected TC-7 cells. MTs appeared to arise from a MT-organizing center near the nucleus, without evidence of MT bundling. These observations provided an initial suggestion that expression of the EMTB constructs bearing multiple GFP moieties did not artifactually alter the MT cytoskeleton.

Measurement of mitotic indices in the cells provided an impression of the impact of the chimeric proteins on progression through mitosis. Cells expressing high levels of GFP-EMTB or 2X-GFP-EMTB indeed exhibited aberrant mitoses. However, cells with lower level expression of 2X-GFPMTB were normal, even though their MTs were sufficiently bright to allow time-lapse fluorescence imaging. This confirmed the utility of these cells for analyzing the behavior of this MAP as well as the dynamics of MTs with bound Ensconsin in live cells.

Association of Ensconsin with MTs at Steady State and During in Vivo Polymerization The observation that MTs in TC-7-2X-GFP-EMTB cells were not bundled allowed for examination of the interaction of Ensconsin with MTs in vivo. Dual time-lapse fluorescence imaging of X-rhodamine labeled MTs and 2X-EMTB-GFP revealed that all MTs in the TC-7 cells contained bound Ensconsin. 2X-GFP-EMTB fluorescence appears diffuse in cells treated with nocodazole for overnight to depolymerize all MTs.

Non Perturbing Label for MTs

To test the hypothesis that 2X- and 3X-GFP-EMTB serve as non-perturbing labels for MTs, we analyzed MT dynamics in clonal cell lines. Rates of growth and shortening in stably transfected cells were similar to those of MTs in nontransfected cells, thus, GFP-Ensconsin chimeric molecule provide a non-perturbing label for MTs while allowing for observation of Ensconsin behavior in living cells.

Extensions of the Technology of Conjugating GFP Multimers to Proteins

Multimers of different GFP mutants have been used to derivatize proteins of interest. To allow simultaneous, sensitive detection of other proteins at the same time as the visualization of GFP multimers, multiple yellow or red-shifted GFP(YFP) were cloned coding sequences onto coding sequences of microtubule-associated protein (MAP) domains. (Faire, et al.) In this derivitization, the Clontech YFP-N1 was used in place of the Clontech GFP-N1 vector. BamHl and HindIII restriction sites were used and placed 3 YFP's adjacent to MAP sequences. Similar experiments were performed placing multiple copies of two different variants of BFP coding sequences adjacent to peroxisome targeting sequences.

This approach can be used with a variety of other mutants of GFP, such as uv-excitable GFP, GFP mutants optimized for efficient expression in a variety of organisms exhibiting different codon bias (such as Drosophila, c elegans, yeast, prokaryotic versions of GFP mutants or naturally occuring organisms other than the jellyfish). The multimerized GFP mutants are sometimes attached at the N-terminus of the protein, and sometimes at the C-terminus.

Since performing original constructs utilizing GFP multimer technology, streamlined and optimized strategies for multimerizing GFP's within the vectors have been developed. For example, various lengths of linker sequences between adjacent GFP-coding sequences in the plasmids have been used. The linker sequences are vital to allow each GFP to fold independently and correctly. The finding that at least 10 amino acids that are hydrophilic and present an extended structure is optimal. Although 5–20 have been tried, bias from experience is 10. Previously, a unique restriction site was used as the point of insertion for each additional GFP. It has been found that using a streamlined approach, in which the DNA encoding each additional GFP (or YFP or other mutant) is always inserted at the Bam Hl site of the vector. One primer contains a Bam Hl site, while the other contains a Bg[I] site. Because Bg[I] and Bam Hl have compatible ends, the site of BgI/Bam insertion is no longer able to be cut by either enzyme. This novel strategy allows us to build up any number of GFP's without generating additional Bam Hl cutting sites; this 'trick' is convenient not only to limit cutting sites (at any stage during the multimerization, only a single Bam Hl cutting site is able to be cut), but to also cut short the process of determining directionally of insertion of each new GFP.

REFERENCES

Block, S. M., et al. (1991) "Visualization of bacterial flagella by video-enhanced light microscopy." *J Bacteriol* 173:933–936;

Bulinski, J. C. and Bossler, A. (1994) "Purification and characterization of ensconsin, a novel microtubule stabilizing protein." *J Cell Science* 107:2839–2849;

Bulinski, J. C. and Borisy, G. G. (1979) "Self-assembly of Hela tubulin and the identification of HeLa microtubule-associated proteins." *Proc Natl Acad Sci USA* 76:293–297;

Chapin, S. and Bulinski, J. C. (1991a) "Non-neuronal 210 kD microtubule-associated protein (MAP4) contains a domain homologous to the microtubule-binding domains of neuronal MAP2 and tau." *J Cell Sci* 98:27–36;

Chapin, S. J., and Bulinski, J. C. (1991b) "Preparation and functional assay of tyrosinated and detyrosinated tubulin." *Methods in Enzymology* 196:254–264;

Cormack, B. P., et al. (1996) "FACS-optimized mutants of the Green Fluorescent Protein (GFP)." *Gene* 173:33–38;

Dickson, R. M., et al. (1997) "On/off blinking behavior of single molecules of Green Fluorescent Protein." *Nature* 388:355–358;

Faire, K. et al. (1999) "E-MAP-115 (Ensconsion) Associates Dynamically with Micro-tubules in vivo and is not a physiological modulator of microtubule dynamics." *Journal of Cell Science* (in press);

Masson, D., and Kreis, T. E. (1995) "Binding of E-MAP-115 to microtubules is regulated by cell cycle dependent phosphorylation." *J Cell Biol* 131:1015–1024;

Nguyen, H. L., et al. (1998) "MAP4 regulates tubulin and microtubule levels in cultured cells.", Manuscript Submitted;

Salmon, E. D., et al. (1998) *Meth Cell Biol* 56:185–214;

Waterman-Storer, C. M. and Salmon, E. D. (1997) "Actomyosin-based retrograde flow of microtubules in the lamella of migrating epithelial cells influences microtubule dynamic instability and turnover and is associated with microtubule breakage and treadmilling." *J Cell Biol* 139:417–434.

What is claimed is:

1. A nucleic acid comprising:
   (a) a first segment which encodes a polypeptide of interest; and
   (b) a second segment encoding at least two Green Fluorescent Proteins, wherein the second segment is attached to one end of the first segment and wherein the nucleic acid encodes a fusion protein comprising the polypeptide of interest linked at one of its termini to at least two Green Fluorescent Proteins.

2. The nucleic acid of claim 1 wherein the second segment is attached to the 5' end of the first segment.

3. The nucleic acid of claim 1 wherein the second segment is attached to the 3' end of the first segment.

4. A vector comprising the nucleic acid of claim 1.

5. A polypeptide encoded by the nucleic acid of claim 1.

6. A fusion protein comprising at least two Green Fluorescent Proteins at one of its termini.

7. A method for detecting the presence of a polypeptide of interest in a living cell which comprises:
  (a) transfecting the cell with a nucleic acid which encodes a fusion protein comprising the polypeptide of interest linked at one of its termini to at least two Green Fluorescent Proteins;
  (b) culturing the transfected cell under conditions permitting expression of the fusion protein; and
  (c) detecting the presence in the cell of fluorescence due to Green Fluorescent Protein, thereby detecting the presence of the polypeptide of interest in the cell.

8. A method for detecting the movement of a polypeptide of interest in a living cell which comprises:
  (a) transfecting the cell with a nucleic acid which encodes a fusion protein comprising the polypeptide of interest linked at one of its termini to at least two Green Fluorescent Proteins;
  (b) culturing the transfected cell under conditions permitting expression of the fusion protein; and
  (c) determining the location in the cell of fluorescence due to Green Fluorescent Protein at a plurality of time points, a difference in location of fluorescence over time indicating movement of the polypeptide of interest, thereby detecting movement of the polypeptide of interest in the cell.

* * * * *